(12) United States Patent
Keller et al.

(10) Patent No.: US 7,120,481 B2
(45) Date of Patent: Oct. 10, 2006

(54) PROBE AND APPARATUS FOR MEASURING CEREBRAL HEMODYNAMICS AND OXYGENATION

(75) Inventors: Emmaneula Keller, Kilchberg (DE); Andreas Nadler, Waedenswil (DE); Peter Niederer, Zuerich (DE)

(73) Assignee: Universitat Zurich, Zurich (CH)

( * ) Notice: Subject to any disclaimer, the term of this patent is extended or adjusted under 35 U.S.C. 154(b) by 317 days.

(21) Appl. No.: 10/333,262

(22) PCT Filed: Jul. 19, 2001

(86) PCT No.: PCT/EP01/08331

§ 371 (c)(1),
(2), (4) Date: Aug. 11, 2003

(87) PCT Pub. No.: WO02/07592

PCT Pub. Date: Jan. 31, 2002

(65) Prior Publication Data

US 2004/0039270 A1   Feb. 26, 2004

(30) Foreign Application Priority Data

Jul. 21, 2000   (EP)   ................................. 00115732

(51) Int. Cl.
*A61B 5/00* (2006.01)
(52) U.S. Cl. ...................................... 600/339; 600/325
(58) Field of Classification Search ................ 600/310, 600/322–325, 337, 339
See application file for complete search history.

(56) References Cited

U.S. PATENT DOCUMENTS

| | | | |
|---|---|---|---|
| 4,223,680 A | | 9/1980 | Jobsis |
| 4,281,645 A | * | 8/1981 | Jobsis ......................... 600/324 |
| 4,784,150 A | * | 11/1988 | Voorhies et al. ............. 600/473 |
| 5,024,226 A | * | 6/1991 | Tan .............................. 600/340 |
| 5,057,695 A | * | 10/1991 | Hirao et al. .................. 600/310 |
| 5,193,544 A | | 3/1993 | Jaffe |
| 5,218,962 A | | 6/1993 | Mannheimer et al. |
| 5,524,617 A | * | 6/1996 | Mannheimer ................ 600/323 |

(Continued)

FOREIGN PATENT DOCUMENTS

GB    2 136 120 A    9/1984

(Continued)

OTHER PUBLICATIONS

Emanuela Keller et al., "Bedside Monitoring of Cerebral Blood Flow in Patients With Acute Hemispheric Stroke", Crit Care Med 2000 vol. 28, No. 2, pp. 511-516.

(Continued)

*Primary Examiner*—Eric F. Winakur
(74) *Attorney, Agent, or Firm*—Nixon Peabody LLP; Donald R. Studebaker

(57) ABSTRACT

A probe and an apparatus for cerebral diagnostics and therapy, in particular for measuring absolute values of regional cerebral flow (CBF) and cerebral oxygenation. The probe is inserted through a burr hole in the skull and comprises illuminating device, light receiving device and a coating encapsulating said illuminating device and said light receiving means. The coating has a longitudinal shape and is adapted to fit through a burr hole in the skull. The coating is further adapted to slide between the skull and the dura, to be inserted into the ventricular system, and/or to be inserted into the cerebral tissue.

28 Claims, 9 Drawing Sheets

U.S. PATENT DOCUMENTS

| | | | |
|---|---|---|---|
| 5,579,774 A * | 12/1996 | Miller et al. | 600/480 |
| 5,632,273 A * | 5/1997 | Suzuki | 600/310 |
| 5,713,352 A * | 2/1998 | Essenpreis et al. | 600/473 |
| 5,916,171 A | 6/1999 | Mayevsky | |
| 6,095,974 A * | 8/2000 | Shemwell et al. | 600/310 |
| 6,353,226 B1 * | 3/2002 | Khalil et al. | 600/310 |
| 6,533,733 B1 * | 3/2003 | Ericson et al. | 600/561 |
| 6,615,061 B1 * | 9/2003 | Khalil et al. | 600/310 |

FOREIGN PATENT DOCUMENTS

| | | |
|---|---|---|
| GB | 2 333 152 A | 7/1999 |
| WO | WO 97 12210 A | 4/1997 |

OTHER PUBLICATIONS

Emanuela Keller et al., "Changes in Cerebral Blood Flow and Oxygen Metabolism During Hypothermia in Patients With Severe Middle Cerebral Artery Infarction", Neurosurg. Focus, vol. 8, May 2000, pp. 1-4.

Jobis, F. F., "Noninvasive inferred monitoring of cerebral and myocardial oxygen sufficiency and circulatory parameters", Science 198; 1264-1267.

I. Roberts, P. Fallon, et al., "Estimation of cerebral blood flow with near infrared spectroscopy and indocyanaingreen", Lancet 342; 1425.

* cited by examiner

PROBE AND APPARATUS FOR MEASURING CEREBRAL HEMODYNAMICS AND OXYGENATION

The present invention relates to a probe and an apparatus for cerebral diagnostics and therapy, in particular for measuring characteristics of cerebral hemodynamics and oxygenation.

BACKGROUND OF THE INVENTION

Early detection and treatment of cerebral ischemia to prevent further neurological damage in patients with severe brain injuries belongs to the most important issues in Neurocritical Care. Further, during neurological and neurologically related surgical procedures it is often desirable to continuously monitor the oxygenation of blood which is supplied to the brain. Near infrared spectroscopy (NIRS) is used for a wide variety of applications including invasive and non-invasive monitoring of cerebral blood flow (CBF) and cerebral oxygenation pattern, i.e. static and dynamic characteristics of cerebral blood and blood flow. The NIRS measurement of blood parameters is based upon the finding that light in the near infrared region penetrates biological tissue and is absorbed and scattered differently by hemoglobin chromophores in the deoxygenated and oxygenated state. Further, the concentration and flow of tracers such as the dye indocyaningreen (ICG) injected in the blood can be measured by NIRS to obtain information on parameters of cerebral hemodynamics, especially cerebral blood flow (CBF), mean transit time of ICG and oxygen metabolism. In pulse oximetry the temporal behaviour of NIRS signals is evaluated to obtain information about the fraction of oxygenated hemoglobin in the arterial blood. Other parameters are the concentration of deoxygenated and oxygenated hemoglobin, the mean transit time, the cerebral blood volume (CBV), cerebral blood flow (CBF) and the tissue oxygen index (TOI). The measurement and evaluation of the aforementioned parameters with NIRS are described in Jobis, F. F., "Noninvasive infrared monitoring of cerebral and myocardial oxygen sufficiency and circulatory parameters", Science 198; 1264–1267 and I. Roberts, P. Fallon, et al., "Estimation of cerebral blood flow with near infrared spectroscopy and indocyaningreen", Lancet 342; 1425.

Non-invasive techniques, e.g. as described in U.S. Pat. No. 4,223,680 or U.S. Pat. No. 5,218,962, use NIRS optodes placed on the head. To obtain information on the chromophores oxyhemoglobin and deoxyhemoglobin in cerebral vessels the detected NIRS signal gained by non-invasive techniques has to be corrected for effects due to light reflection and scattering by and in extracerebral tissue, i.e. skin and bone. The apparatus described in U.S. Pat. No. 4,223,680 therefore comprises a reference detector which detects light reflected or scattered back to the location of the light emitting optode. The reference signal is then used to correct the measured intensity for extracerebral tissue effects. The apparatus of U.S. Pat. No. 5,218,962 comprises two light emitting elements directing light through different regions of tissue and a photodetector detecting light travelling through both regions. The difference of the measured intensities represents how much the oxygen saturation of the first region differs from the second region, i.e. only relative blood parameters can be obtained. Due to the need for correction for extracerebral tissue effects non-invasive techniques are able to provide indirect information on blood parameters only.

With invasive techniques direct access to the brain and elimination of extracerebral contamination is gained through a burr hole in the skull, and a sensor which optically measures oxygenation without artifacts caused by skin and bone can then be inserted through such a burr hole. A sensor capable of monitoring several parameters instantaneously is disclosed in U.S. Pat. No. 5,916,171. Several signal guides for electrical signals and a single light guide are arranged in a housing which is inserted in a burr hole having approximately the same diameter as the housing. The light guide and the electrodes terminate vertically at the brain tissue. UV and red light is coupled into the single light guide to measure relative changes of the blood flow velocities by analyzing the signal reflected back into the same light guide using Laser Doppler flowmetry. With this arrangement only relative parameters of flowing blood can be analyzed as the signal coming from static tissue components are not detectable in Laser Doppler flowmetry. Furthermore by Laser Doppler flowmetry only values of very small areas (about 1 $mm^2$) are obtained. Futher, the probe is merely inserted into the burr hole and stabilized by the skull bone which can lead to brain injuries or artifacts in the measurements when the patient moves. It is therefore not suited for a long-term measurement. Monitoring regions of tissue other than those of the burr hole is not possible. As the probe comprises a complex arrangement of a plurality of sensors its manufacturing costs are high and it is therefore not suited as a throw away article. Products that contact the brain, however, should be throw away articles as sterilizing is often not sufficient to exclude a potential infection risk.

A sensor for measuring cerebral oxygen availability epidurally, i.e. between dura and skull bone, by optical reflectance is disclosed in U.S. Pat. No. 5,024,226. A pair of light emitting diodes (LED) and a photodetector are encapsulated by a coating and connected electrically to a power supply respectively a signal analyzer by a flexible wiring. The sensor tip including the diodes and the photodetector is inserted through a burr hole in the skull and maneuvered between dura and skull bone to a region chosen for the measurement.

It is therefore an object of the present invention to provide a probe and an apparatus for measuring absolute values of regional cerebral flow and cerebral oxygenation through a burr hole in the skull by optical reflectance which can be manufactured at relatively low cost and is therefore suited as a throw away article.

SUMMARY OF THE INVENTION

The above and other objects of the present invention are achieved by a probe set forth in accordance with the present invention. Preferred embodiments are described in the description and the drawings.

The inventive probe may be used for any invasive method for cerebral diagnostics and therapy. It may be used as a probe for subdural measurements, as a ventricular probe or as a intraparencymatic probe. The coating is therefore adapted to slide between the skull and the dura, and/or to being inserted into the ventricular system, and/or to being inserted into the cerebral tissue. When used in diagnostics and therapy, the probe may be used to transfer and release a substance into the cerebral tissue and/or into the ventricular system.

The illuminating means may be active, i.e. may comprise light emitting means such as a diode and/or a laser, or passive, i.e. transmit light from an external light source to the location of measurement. If the illuminating means emit light actively, they are powered electrically. The light receiving means may be active or passive, too. In the active case they detect light in the location of measurement and generate an electric signal which is transmitted to an evaluating means. In the passive case, the receiving means are suited to receive light from the location of measurement and to transmit it to an external detector.

This probe uses a passive illuminating and receiving device and avoids electric components within the probe. The use of light emitting diodes for in situ generation of light, as for example in U.S. Pat. No. 5,024,226, has several problematic aspects. The emission spectrum of a LED is fixed, thus a given probe cannot be adapted for monitoring different parameters with their specific wavelengths. For monitoring a given number of different parameters the same number of LEDs has to be provided within the probe, requiring a certain space, thus increasing the probe dimensions. A LED emits a broad spectrum of wavelengths, thus no sharp working wavelengths can be employed. The LEDs have to be powered electrically, i.e. an electrical wiring has to be guided in the skull.

An improper insulation of the wiring can cause electrical shortcuts which may result in brain damage. Further, the signals transferred to the analyzer are influenced by other electrical equipment, leading to wrong results. The emission characteristics of the LED and the detection efficiency of the photodetector are affected by changes of the temperature, but drift compensation or temperature stabilization in situ is not possible. These problems are avoided by said preferred embodiment of the inventive probe. Especially, electrical signaling in the skull region is avoided. Further, the probe can easily be adapted to different wavelengths. A further advantage is that the probe can be manufactured at low cost due to the absence of electronic equipment within the probe.

The preferred inventive probe uses at least two optical transmission means each comprising one or more optical fibers, the transmission means preferably being a fiber bundle. The first transmission means transmit light preferably in the near infrared spectral range from their proximal end to their distal end, i.e. from a light source to the patient's head. The second transmission means transmit light from their distal end to their proximal end, i.e. from the patient's head to a detection unit. The transmission means are preferably arranged substantially parallel to each other. They are encapsulated by a coating that forms an elongated flat structure. The distal termination of each of the optical transmission means is connected to deflection means encapsulated by the same coating for deflection of light transmitted by the transmission means from the direction of transmission, preferably by an angle of 60 to 120°. Preferably the light is deflected by approximately 90°. with respect to the direction of transmission, directing light from a propagation direction parallel to the dura vertically into the brain tissue. The distance of the deflection means, acting with the respective transmission means as emitting and receiving optodes, determines the probing depth, i.e. the depth up to which photons penetrate the tissue and are scattered back, thus the depth of the tissue region monitored. As optical fibers are small in diameter and deflection means can be manufactured small in size, e.g. by a mirror, preferably a prism with a few millimeters edge length connected to the fiber endings or by fiber endings being inclined, a probe with a width of preferably less than about 20 mm and a thickness less than about 5 mm for a minimal invasive measurement is provided. The coating, preferably a silicone rubber or polyurethane material, fixes the spatial arrangement of transmission and deflection means and enables by a certain stiffness at least in its axial direction maneuvering of the probe within the head. The coating also seals the components from moisture and other environmental factors. Further, the coating smoothly rounds the edges and corners of the probe which prevents injury of the brain when sliding between dura and brain tissue or dura and bone. The coating is at least in the region of the entrance respectively exit of the deflection means optically transmissive to light at the wavelengths used.

For use, the proximal termination of the first transmission means is connected to a light source emitting at one or more wavelengths, and light is directed through the first transmission and deflection means into the brain tissue where it is reflected and/or scattered by tissue components. As the optical fibers are generally able to transmit in a broad spectral range, the same fibers can be used for illumination with different wavelengths in the infrared range associated with specific chromophores in the blood, e.g. oxyhemoglobin, deoxyhemoglobin, ICG. Preferably a glass or quartz fiber having a diameter of about 50 to 100 µm is used. Preferably the transmission respectively comprise a bundle of 300 to 600 fibers each. For example, a wavelength of 782 nm is used to monitor the ICG concentration while oxygenation of hemoglobin is monitored at 908 and/or 857 nm.

When in use, the proximal termination of the second transmission means is connected to a photodetector whose output signal is analyzed by a evaluation means, e.g. a computer. Light reflected and/or scattered by brain tissue is directed into the second transmission means by the second deflection means picking up light coming from a direction approximately normal to the direction of transmission within the fiber. First and second deflection means are directed towards the same direction approximately. The photodetector being outside the body has the advantage that it can be stabilized against temperature drift. Further, as it is part of the permanent analyzing system and does not have to be a low cost product, detectors with high detection efficiency, e.g. photomultipliers or avalanche diodes can be used. Thus the intensity of emitted light can be reduced maintaining a desired signal to noise ratio. For example, it is illuminated at a 1 kHz repetition rate, 50 ns pulse duration and a mean laser power of 1 mW.

The optical probe can be combined with a pressure sensor for intracranial pressure measurement and signal transfer means connected to it for transmitting signals containing pressure information to a pressure signal analyzer. Thereby the following parameters can be monitored simultaneously by inserting one probe in the subdural space through a single burr hole in the skull: oxyhemoglobin, deoxyhemoglobin, means cerebral arterial oxygen saturation $SaO2_{cerebral}$, mean transit time of ICG $mtt_{ICG}$, cerebral blood flow CBF and cerebral blood volume CBV.

The inventive apparatus comprises an inventive probe, light emitting means, light detecting means and evaluation means. For example, a standard NIRS system used for non-invasive oximetry can be combined with the inventive probe. The light emitting means, preferably one or more diode lasers or a tunable laser, e.g. a dye laser, are coupled with the proximal end of the first transmission means, such that emitted light at one or more wavelengths is transmitted to the brain tissue. With an assembly of beamsplitters or bandpass filters light from different light sources can be coupled into common fibers of the first transmission means. The working wavelengths respectively light sources are changed dependent on which wavelength is needed for the measurement of the chromophores in the blood. Alternatively, for each of the preferably three wavelengths a separate fiber bundle can be provided having the advantage of easier alteration of the working wavelength and the disadvantage of increase of the number of fibers needed for a given illumination intensity leading to an increase in width or thickness of the probe.

The light detecting means, preferably a photomultiplier, are coupled with the proximal end of the second transmission means. Bandpass or other optical filters for the suppression of undesired signal components can be arranged in the transmission path.

The evaluation means for the evaluation of the detected signals preferably comprise a computer with evaluation routines.

BRIEF DESCRIPTION OF THE DRAWINGS

Some of the objects and advantages of the present invention have been stated, others will appear when the following description is considered together with the drawings in which

FIGS. 1 and 2 show a probe 1 comprising a bundle of first optical fibers 4 as first transmission means 2 and a bundle of second optical fibers 5 as second transmission means 3. The fibers 4, 5 are aligned substantially parallel to each other. The distal end 15 of the first transmission means 2 is coupled to first deflection means 6, a prism 8, by the first optical fibers 4 being connected to one face of the prism 8. Thereby an incoming light beam 30 is deflected from a direction A corresponding to the direction of the first or second fibers 4, 5 into a direction B approximately normal to the plane 53 defined by the first and second transmission means 2, 3 respectively fibers 4, 5. In the same way the distal end 16 of the second transmission means 3 is coupled to second deflection means 7, a prism 9, by the second optical fibers 5 being connected to one face of the prism 9. Thereby light 31 coming from the outside from a direction B is deflected into the direction A and into the second fibers 5. The face of the prisms 8, 9 oriented at 45°. with respect to the fibers 4, 5 acts as a mirror 10, 11, whose reflectance may be enhanced by a reflecting coating. The distance D1 of the first and second deflection means 8, 9 is fixed and amounts to 35 mm, generally 10 to 50 mm. The aforementioned components are encapsulated by a soft coating 12 which forms a body with round corners having a width W of approximately 7 mm, generally less than 20 mm, and a thickness T of 2 mm, generally less than about 5 mm. This body enables sliding of the probe 1 between dura and brain tissue without damaging or compressing the brain, as shown in FIGS. 8 and 9. The coating has optical windows 13, 14 in the region of the exits of the deflection means 6, 7 transmitting the emitted and reflected photons.

FIG. 3 shows the transmission paths of an inventive probe, e.g. that of FIGS. 1 and 2. The proximal end 21 of the first transmission means 2, comprising a bundle of optical fibers 4 of about 1.5 $mm^2$ sectional area, is split in three sub-paths of about 0.5 $mm^2$ sectional area that are terminated by plugs 18, 19, 20 for coupling with external light sources of three different wavelengths (not shown). The proximal end 22 of the second transmission means 3, comprising a bundle of optical fibers 5 of about 1.5 $mm^2$ sectional area, terminates in a plug 23 for coupling with a photodetector. The first and second transmission means are guided in a common cable of 1 to 2 m length L2. The probe 1 as such, i.e. the part adapted to be introduced into the patient's skull, has a length L1 of about 20 to 30 cm. The distal ends 15, 16 of the first and second transmission means 2, 3 are coupled with deflection means 6, 7 having a distance D1 of 35 mm as described above.

FIG. 4 shows an inventive apparatus comprising an inventive probe 1, e.g. as shown in FIGS. 1 and 2, an NIRS respectively oximetry system 26 and a computer 29 as controlling and evaluating unit 27, 28. Via the first transmission means 2 the probe is connected to the exit of the light source 24 of the system 26. The emission of light (wavelength, pulse width and repetition frequency, power) is controlled by the controlling unit 27. The scattered light is guided by the second transmission means 3 to the photodetector 25, whose output signal is evaluated by the evaluating unit 28.

FIGS. 5 and 6 show an inventive probe 32 integrated in a ventricular catheter in a plan view respectively an axial cross section. The catheter comprises a flexible tube 33 defining a channel 36 with 1 to 2 mm diameter and having openings 34 in the tube walls through which access to brain tissue is gained via the channel 36. First and second transmission 37, 38 and deflection means 39, 40 are integrated in the tube walls proximate to the openings at about 15 to 30 mm distance to the catheter tip. The distance D2 of first and second deflection means 39, 40 is about 15 mm resulting in a probing depth of approximately 15 mm. As the tube walls are less than 1 mm thick, preferably about 0.5 mm, the deflection means 39, 40 are realized by cutting the terminating faces of the optical fibers 41 constituting the transmission means 37, 38 with an inclination of approximately 45° with respect to the fiber direction. The inclined face 42 serves as a mirror to deflect light with about 90° from or into the fiber. With this probe 32 monitoring of parameters by NIRS techniques can be combined with analytical or therapeutic techniques, for example cerebrospinal fluid analysis and drainage, requiring direct access to deeper brain areas, especially in ventricles. The probe 32 may further transfer and release a substance into the cerebral tissue and/or into the ventricular system.

FIGS. 7A, B show an inventive probe 1 with an additional pressure sensor 43. The probe 1 with first and second transmission means 2, 3 and deflection means 6, 7 encapsulated by a soft coating 12 has been described before. A pressure sensor 43 having a signal guide 44 encapsulated by coating 12' is attached to or made in a single piece with the probe 1. For example, as shown in FIG. 7A, a standard pressure probe can be equipped with an inventive probe, whereby the respective coatings 12, 12' are attached to each other without forming sharp edges.

Figures 1, 2:
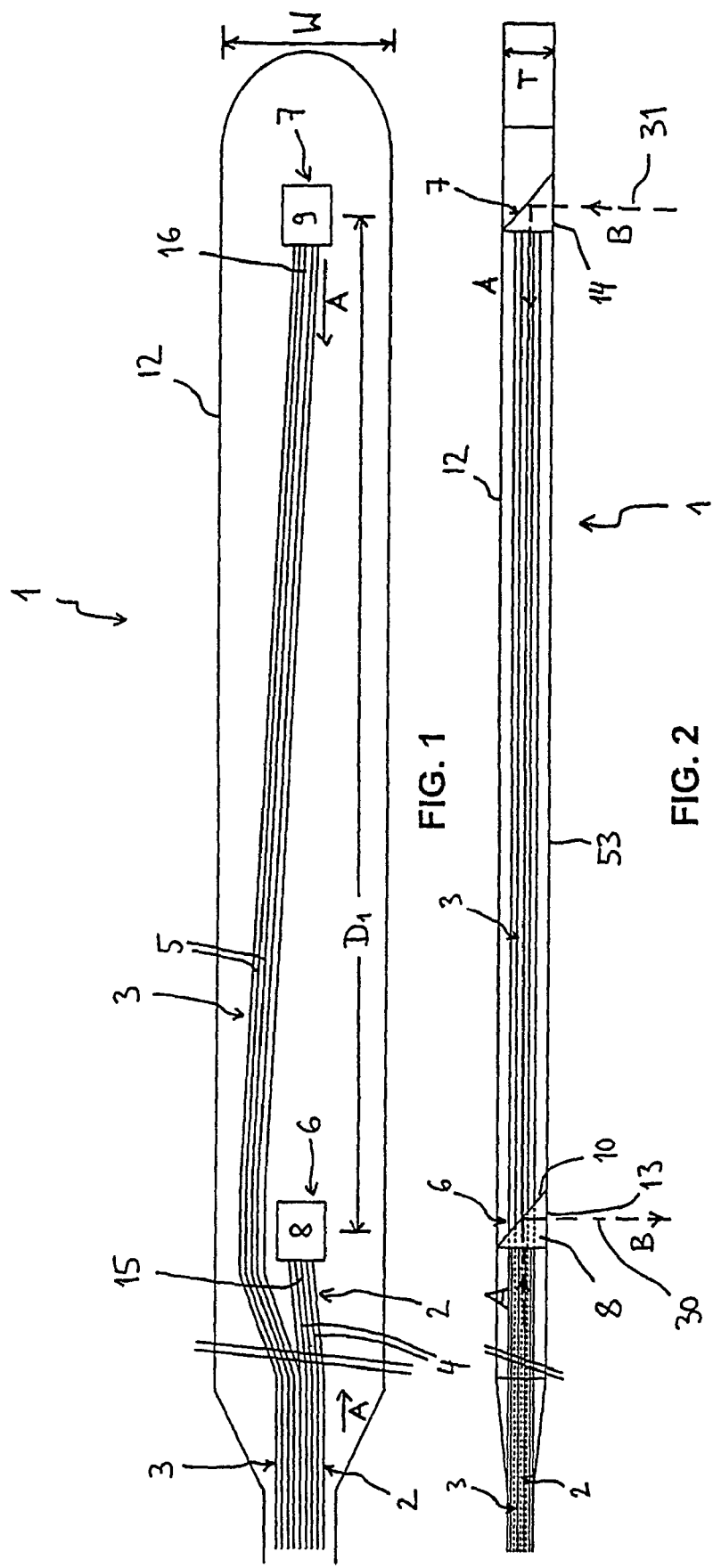
FIG. 1 shows a plan view of an inventive probe.
FIG. 2 shows a side view of the inventive probe of FIG. 1.
Figure 3:
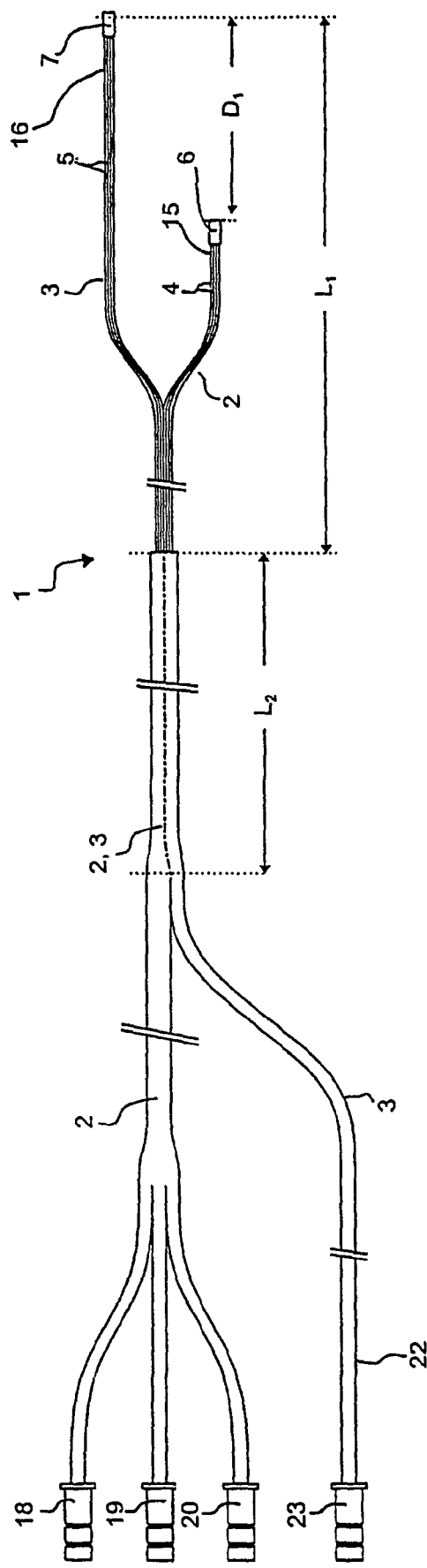
FIG. 3 shows the transmission paths of an inventive probe.
Figure 4:
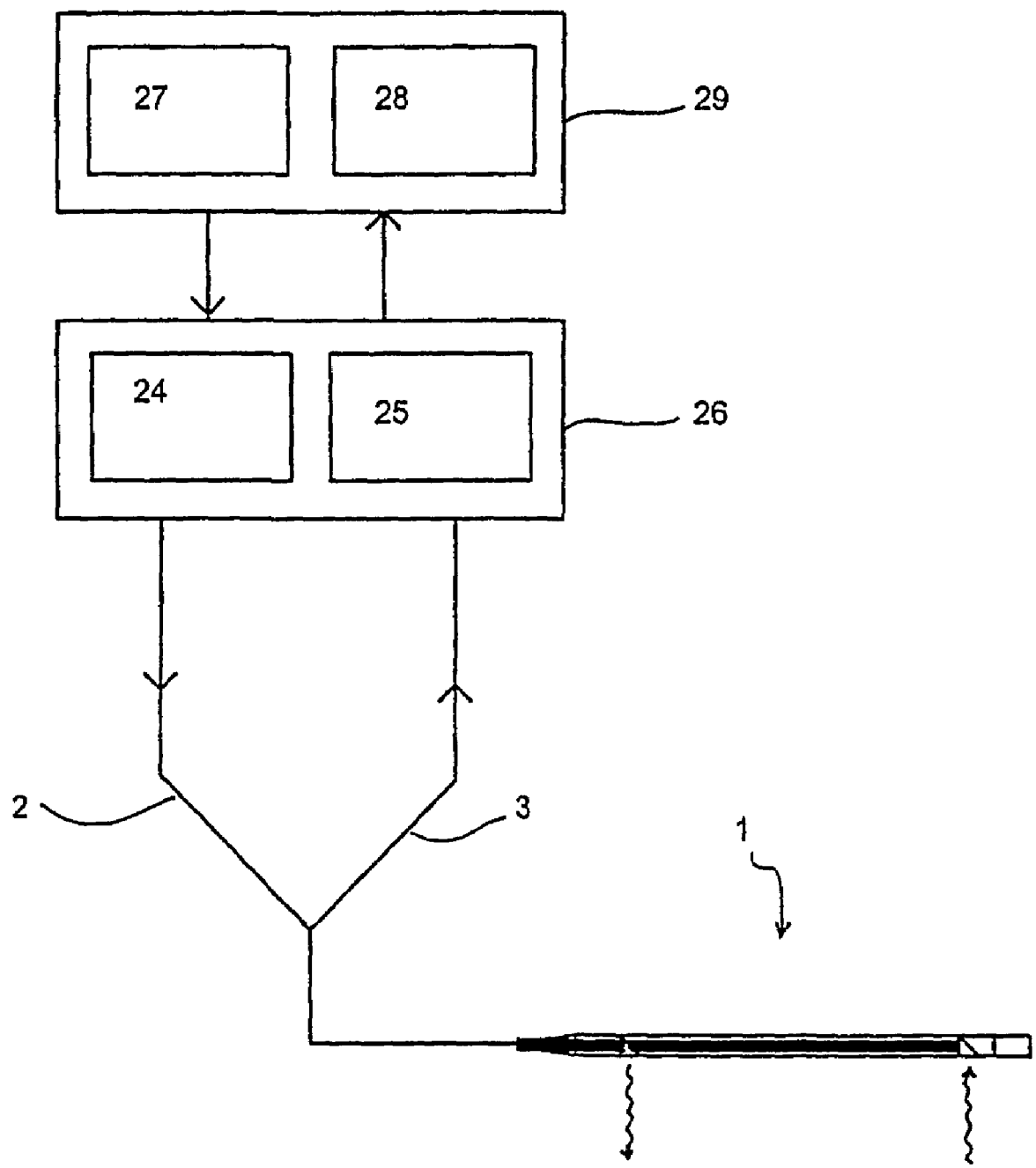
FIG. 4 shows an inventive apparatus.
Figure 5:
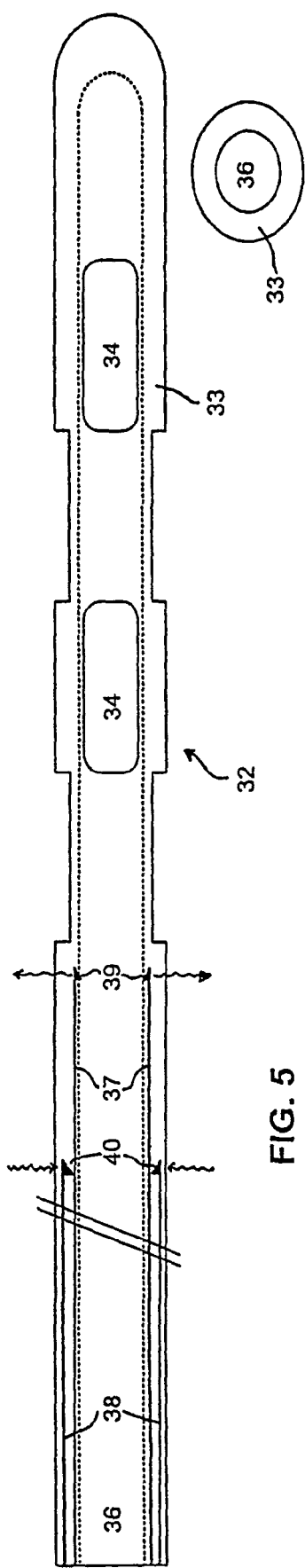
FIG. 5 shows a plan view of an inventive probe integrated in a ventricular catheter.
Figure 6:
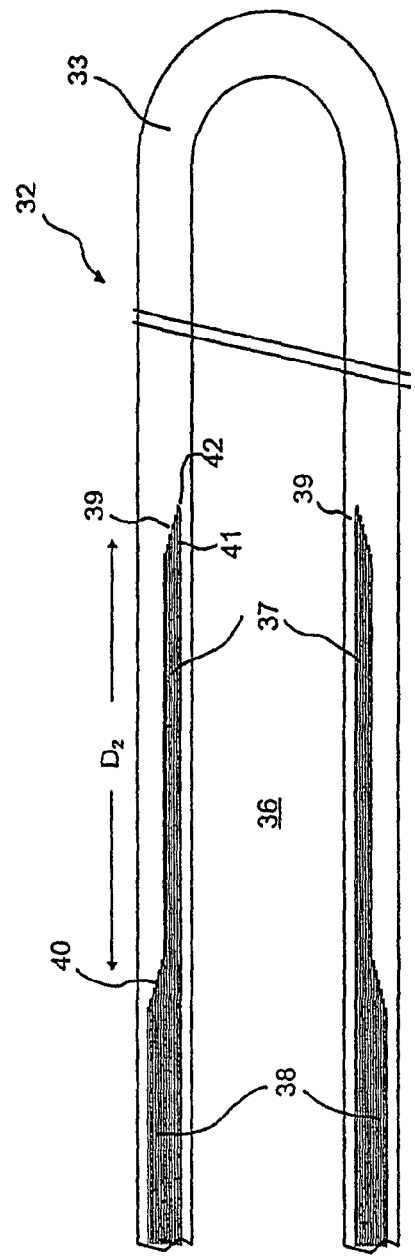
FIG. 6 shows an axial cross section of the probe of FIG. 5.
Figure 7A:
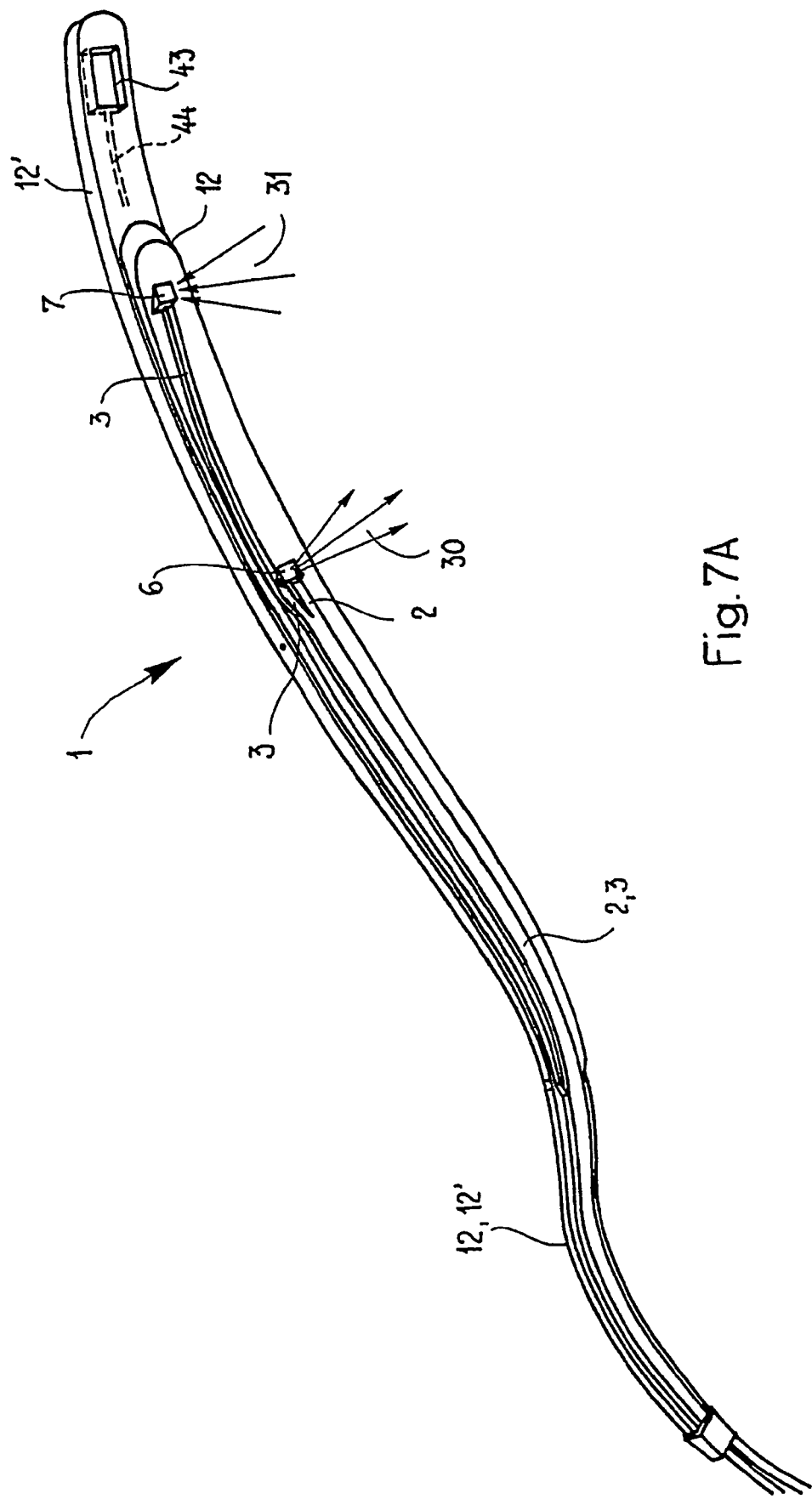
FIGS. 7A, B show an inventive probe with an additional pressure sensor.
Figure 7B:
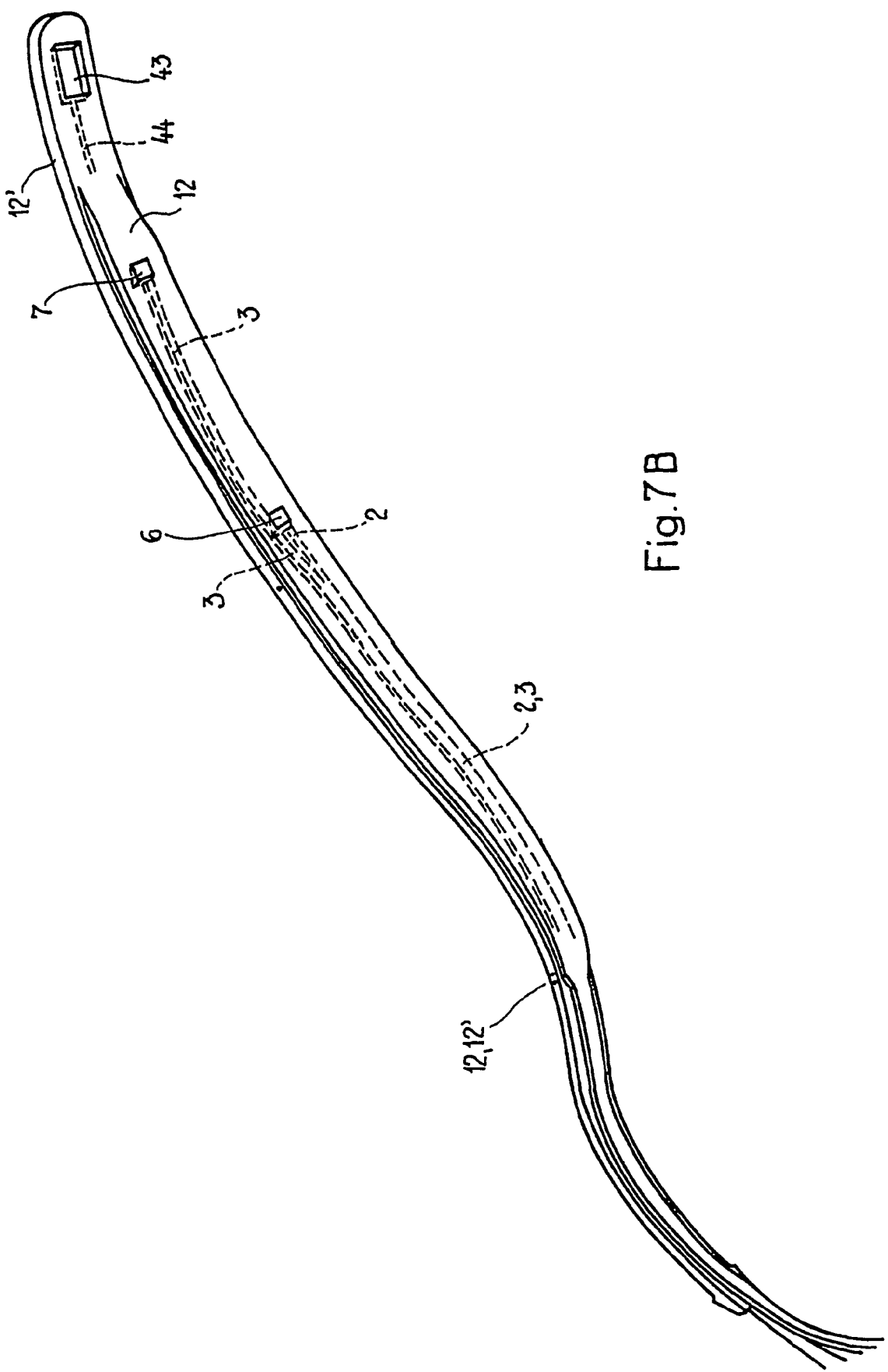

Alternatively, as shown in FIG. 7B, the pressure sensor is an integral part of the inventive probe, encapsulated by a common coating 12, 12'. The probe thus enables simultaneous monitoring of cerebral hemodynamics and oxygenation as well as pressure through a single probe and a single burr hole in the scull.

Figure 8:
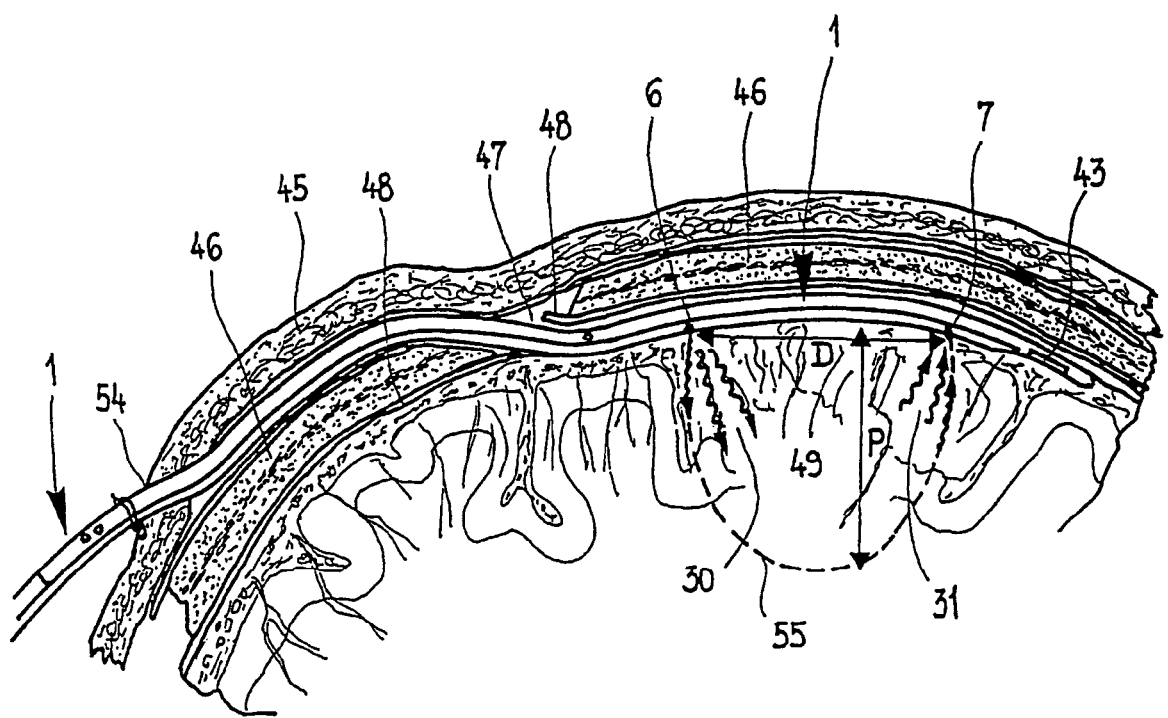
FIG. 8 shows a saggital view of an inventive probe inserted in the subdural space.
Figure 9:
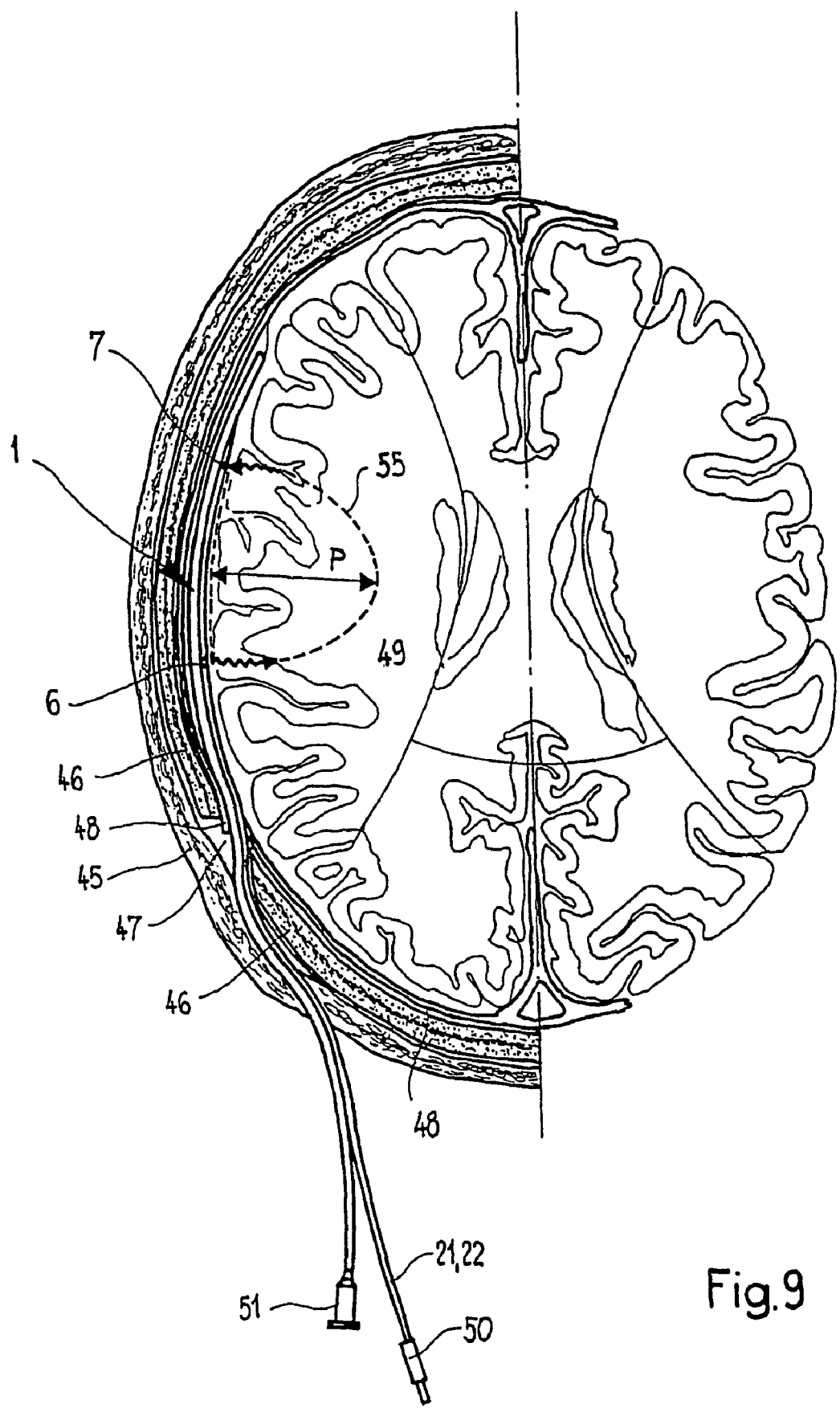
FIG. 9 shows a coronar view of an inventive probe inserted in the subdural space.

FIGS. 8 and 9 show different views of an inventive subdural probe 1 with optical probing and a pressure sensor 43 as shown in FIG. 7 inserted through a burr hole 47 in the skull bone 46 between dura 48 and brain tissue 49. As shown, the probe is first guided through a cut 54 in the skin 45, then through the burr hole 47 spaced from the cut 54, thereby minimizing the infection risk by preventing direct contact of brain tissue with the ambient air during long-term monitoring. Light 30 is deflected by the first deflection means 6 into the brain tissue 49, traveling substantially normal to dura 48 or brain surface where it is absorbed, reflected or scattered. Due to reflection and scattering a part 31 of the light is deviated to the second deflection means 7 and coupled into the second transmission means. The area 55 reached by light emitted by the emitting optode and received by the receiving optode having a distance D is sketched in dashed lines. The penetration or probing depth P is the maximum depth from where photons are received. With a distance D of 35 mm the white brain matter can be investigated. The proximal ends 21, 22 of the optical transmission means and of the pressure signal guide terminate in different plugs 50, 51 to be connected with oximetry respectively pressure monitoring systems (not shown).

Figure 10:
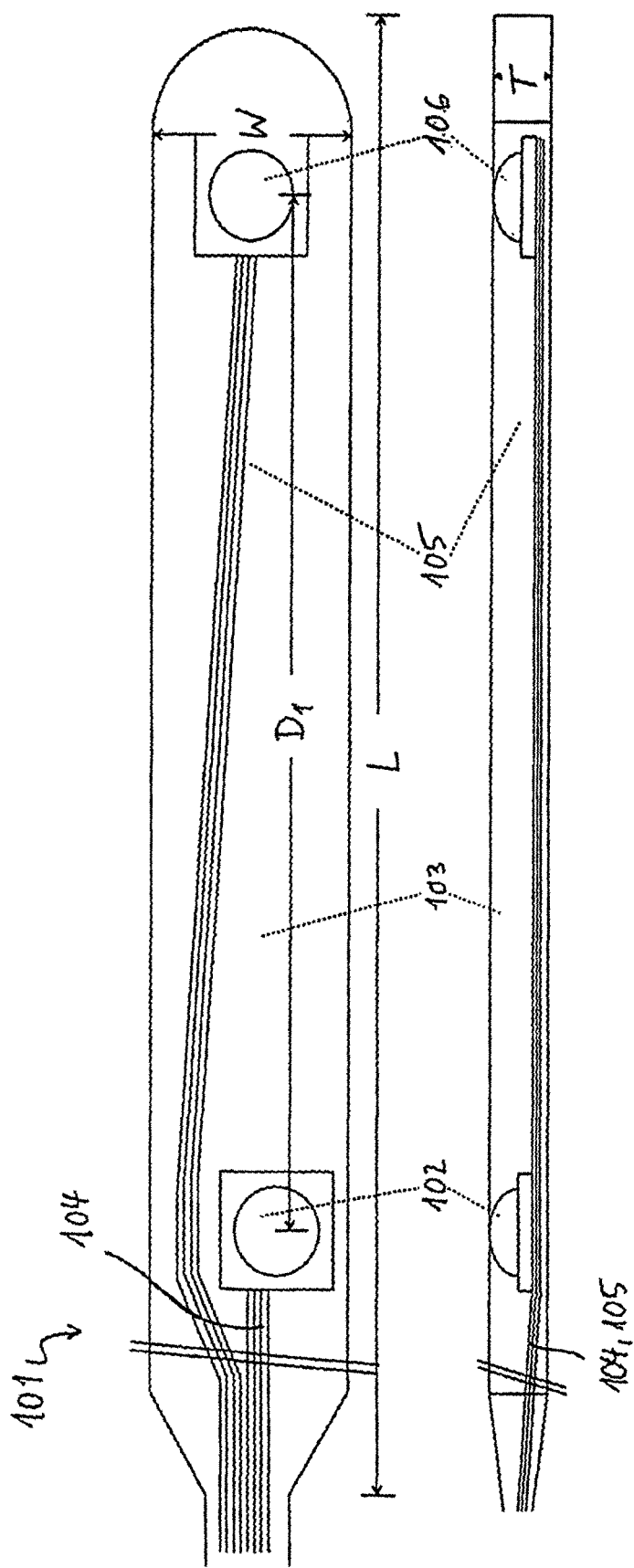
FIG. 10 shows a plan view and a side view of another inventive probe.

FIG. 10 shows in its upper part a plan view and in its lower part a side respectively sectional view of another inventive probe 101 with active generation and detection of light. Light emitting means 102, preferably a diode laser, and light detecting means 106, preferably a receiver diode, are encapsulated by a coating 103, which is preferably made of silicone. The light emitting means 102 are connected via an electrical wiring 104 to an external power supply and/or control unit. The light detecting means 106 are connected via an electrical wiring 105 to an external evaluation system for evaluation of the signals generated by the detecting means 106. The probe 101 is adapted to subdural measurements and has a total length L of about 250 mm, a width W of about 7 mm, and a height T of about 2 mm. The distance D1 between the light emitting and detecting means 102, 106 is about 35 mm.

The invention claimed is:

1. A probe for cerebral diagnostics and/or therapy, in particular for measuring characteristics of cerebral hemodynamics and oxygenation by optical reflectance, comprising
    illuminating means comprising first optical transmission means including at least one first optical fiber, and first deflection means coupled to the first optical transmission means for deflection of transmitted light into a direction other than the direction of light transmission within the first optical transmission means;
    light receiving means comprising second optical transmission means including at least one second optical fiber, and second deflection means coupled to the second optical transmission means for deflection of light into the second optical transmission means, the light coming from a direction other than the direction of light transmission within the second optical transmission means, wherein the first and second deflection means are located at a distance (D1) from each other of 20 to 50 mm;
    a coating encapsulating said illuminating means and said light receiving means, said coating having a longitudinal shape and being adapted to fit through a burr hole in the skull, said coating further being adapted to at least one of the following: sliding between the skull and the dura, being inserted into the ventricular system, being inserted into the cerebral tissue.

2. The probe according to claim 1, wherein the coating is made of silicone rubber or polyurethane.

3. The probe according to claim 1, having a width (W) less than about 20 mm, and a thickness (T) less than about 5 mm.

4. The probe according to claim 1, further comprising a pressure sensor and signal transfer means connected to said pressure sensor for transmitting signals containing pressure information.

5. The probe according to claim 1, further comprising means for the transfer and release of a substance into the cerebral tissue and/or into the ventricular system.

6. The probe according to claim 1, wherein the first and second deflection means deflect light into/from a direction (B) substantially vertical to the direction (A) of light propagation in the transmission means.

7. The probe according to claim 1, wherein the distance (D1) between the first and second deflection means is 30 to 40 mm.

8. The probe according to claim 1, wherein the first and second deflection means include a mirror oriented at approximately 45° with respect to the direction of the first and second optical transmission means.

9. The probe according to claim 8, wherein the mirror is a prison.

10. The probe according to claim 1, wherein the face of the at least one first or second fiber at the distal end of the first and second transmission means is oriented at approximately 45° with respect to the direction of light propagation (A) within the first respectively second optical transmission means.

11. The probe according to claim 1, wherein the first and second optical transmission means each include a plurality of first and second optical fibers, the fibers being arranged in a common plane.

12. The probe according to claim 1, wherein the coating includes an optical window in the region of the first and second deflection means.

13. The probe according to claim 1, wherein the first and second optical fibers are suited to transmit light within the near infrared region of 700 to 1300 nm spectral range.

14. The probe according to claim 1, having a width (W) less than about 10 mm, and a thickness (T) less than about 2 mm.

15. The probe according to claim 1, wherein the first and second optical fibers are suited to transmit light within the near infrared region of 750 to 950 nm spectral range.

16. A probe for cerebral diagnostics and/or therapy, in particular for measuring characteristics of cerebral hemodynamics and oxygenation by optical reflectance, comprising
    illuminating means comprising at least one light emitting device (102);
    light receiving means comprising at least one light detecting device (106);
    wherein the illuminating means and the light receiving means are located at a distance (D1) from each other of 20 to 50 mm;
    a coating encapsulating said illuminating means and said light receiving means, said coating having a longitudinal shape and being adapted to fit through a burr hole in the skull, said coating further being adapted to at least one of the following: sliding between the skull and the dura, being inserted into the ventricular system, being inserted into the cerebral tissue.

17. Probe according to claim 16, wherein the light emitting device is powered via first electric wiring and the light detecting device generates an electric signal transmitted via a second electric wiring.

18. The probe according to claim 16, wherein the light emitting device comprises a light emitting diode (LED) or a diode laser.

19. The probe according to claim 18, wherein the light emitting device emits a light in the near infrared region of 700 to 1300 nm spectral range, and the light detecting device comprises a receiver diode.

20. The probe according to claim 16, wherein the illuminating means comprise a plurality of light emitting devices.

21. The probe according to claim 16, wherein the coating is made of silicone rubber or polyurethane.

22. The probe according to claim 16, having a width (W) less than about 20 mm and a thickness (T) less than about 5 mm.

23. The probe according to claim 16, having a width (W) of 5 to 10 mm, and a thickness (T) of about 2 mm.

24. The probe according to claim 16, further comprising a pressure sensor and signal transfer means connected to it for transmitting signals containing pressure information.

25. The probe according to claim 16, further comprising means for the transfer and release of a substance into the cerebral tissue and/or into the ventricular system.

26. The probe according to claim 16, wherein the illuminating means and the light receiving means are located at a distance (D1) from each other of 30 to 40 mm.

27. The probe according to claim 16, wherein the coating includes an optical window.

28. The probe according to claim 16, wherein the light emitting device is capable of emitting at wavelengths at about 782 nm, 857 nm and 908 nm.

* * * * *